United States Patent
Böhm et al.

(10) Patent No.: US 11,207,029 B2
(45) Date of Patent: Dec. 28, 2021

(54) METHOD FOR DENOISING TIME SERIES IMAGES OF A MOVED STRUCTURE FOR MEDICAL DEVICES

(71) Applicants: Stefan Böhm, Oberasbach (DE); Boris Stowasser, Erlangen (DE)

(72) Inventors: Stefan Böhm, Oberasbach (DE); Boris Stowasser, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 1189 days.

(21) Appl. No.: 15/478,853

(22) Filed: Apr. 4, 2017

(65) Prior Publication Data

US 2017/0281093 A1    Oct. 5, 2017

(30) Foreign Application Priority Data

Apr. 5, 2016 (DE) .......................... 102016205603.4

(51) Int. Cl.

| | |
|---|---|
| *A61B 6/00* | (2006.01) |
| *G06T 5/00* | (2006.01) |
| *G06T 7/00* | (2017.01) |
| *A61B 5/00* | (2006.01) |
| *G06T 7/11* | (2017.01) |

(52) U.S. Cl.
CPC .......... *A61B 5/7214* (2013.01); *A61B 5/0075* (2013.01); *A61B 5/725* (2013.01); *A61B 5/7225* (2013.01); *A61B 6/487* (2013.01); *A61B 6/5264* (2013.01); *G06T 5/002* (2013.01); *G06T 7/0012* (2013.01); *G06T 7/11* (2017.01); *A61B 2576/00* (2013.01); *G06T 2207/10016* (2013.01); *G06T 2207/10048* (2013.01); *G06T 2207/10116* (2013.01); *G06T 2207/20182* (2013.01)

(58) Field of Classification Search
CPC ... A61B 5/0075; A61B 5/7214; A61B 5/7225; A61B 5/725; A61B 6/487; A61B 6/5264; A61B 2576/00; G06T 5/002; G06T 7/0012; G06T 7/11; G06T 2207/10016; G06T 2207/10048; G06T 2207/10116; G06T 2207/20182; G16H 30/40
USPC ....................................................... 382/128
See application file for complete search history.

(56) References Cited

U.S. PATENT DOCUMENTS

2009/0285461 A1* 11/2009 Bohm ...................... G06K 9/40
                                                          382/128

OTHER PUBLICATIONS

Hensel et al., "Noise Reduction with Edge Preservation by Multiscale Analysis of Medical X-Ray Image Sequences", Proceedings BVM 2005, Heidelberg, Germany, Mar. 13-15, 2005, p. 55-59. (Year: 2005).*

(Continued)

*Primary Examiner* — Boniface N Nganga
(74) *Attorney, Agent, or Firm* — Lempia Summerfield Katz LLC

(57) ABSTRACT

Embodiments provide a method for denoising time series images of a moved structure for a medical device. A movement detector detects the moved structure. The movement detector obtains a measurement of the similarity of two images that each represent the same section of the moved structure. The two images originate from two different time series images. A ratio between spatial and temporal denoising is defined for the section as a function of the measurement of the similarity.

14 Claims, 2 Drawing Sheets

(56) References Cited

OTHER PUBLICATIONS

Grigat, "Motion Detection for Adaptive Spatio-temporal Filtering of Medical X-Ray Image Sequences", Proceedings MIUA, Bristol, U.K., Jul. 19-20, 2005, p. 219-222 (Year: 2005).*
Bührle E. et al.: "Mehrstufige zeit-und bewegungsabhängige Rauschreduktion in Echtzeit mittels CUDA"; Bildverarbeitunq für die Medizin 2009, Springer, pp. 464-468; 2009.
Martin S. et al.: "Bewegungsdetektion und zeitliche Filterung auf Bandpassbildern unter Verwendung mehrerer vorangegangener Bilder"; The IP.com Journal, vol. 8 Issue 18, Dokument IPCOM000166286D, 2008.
Schoonenberg, G. et al.: "Adaptive spatial-temporal filtering applied to x-ray fluoroscopy angiography," Medical Imaging 2005, Proc. Of SPIE, vol. 5744, pp. 870-878; 2005.
Shylaja, S. L. et al.: "Adaptive and Recursive Based Spatio-Temporal Filtering for Video Denoising with RWT Transformation," Annual IEEE India Conference (INDICON), pp. 1-6; 2015.
Zlokolica, Vladimir et al.: "Wavelet-based denoising for 30 OCT images" In: Optical Engineering+ Applications. International Society for Optics and Photonics, pp. 66960P-1 to 66960P-11; 2007.

\* cited by examiner

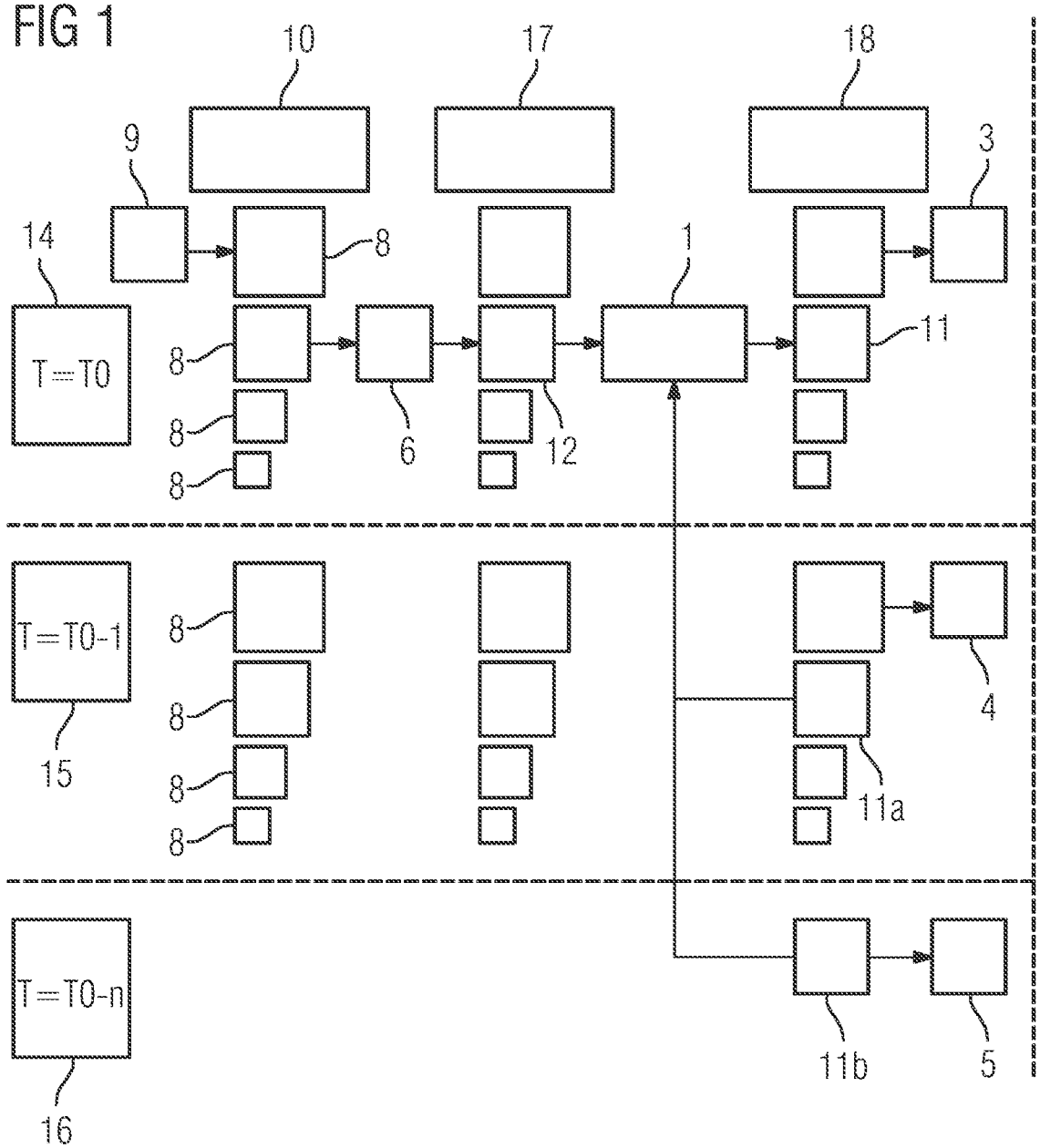

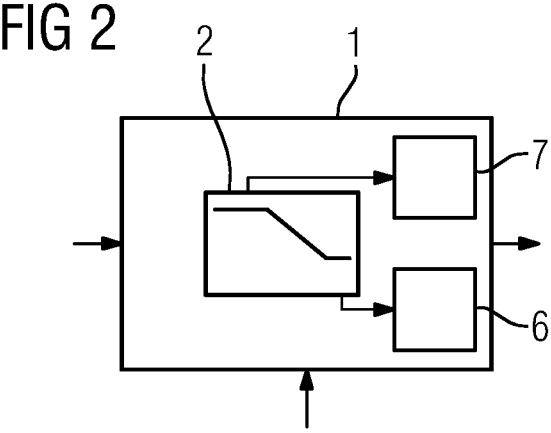
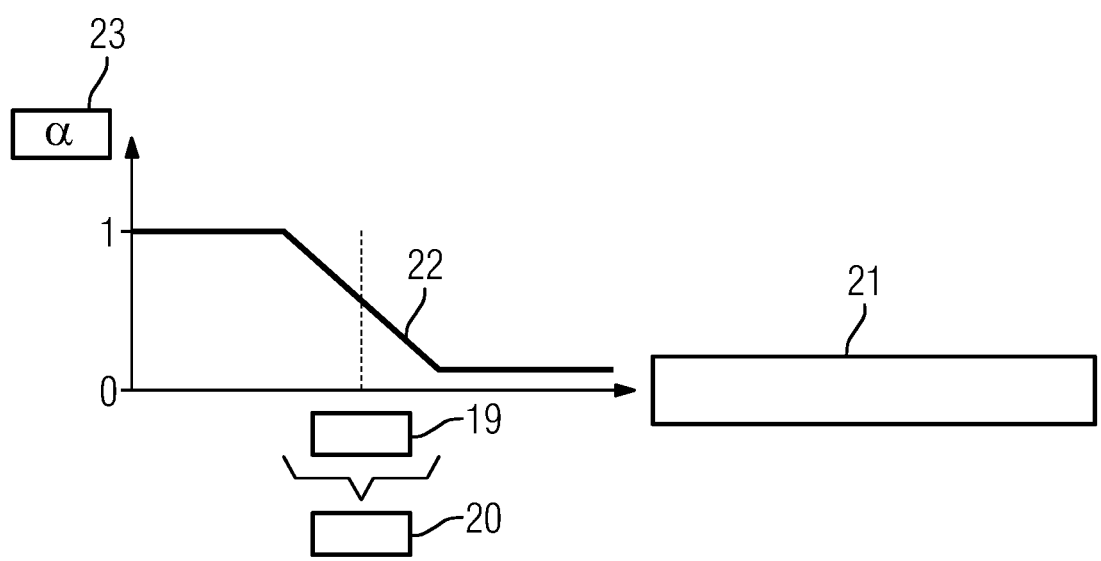

METHOD FOR DENOISING TIME SERIES IMAGES OF A MOVED STRUCTURE FOR MEDICAL DEVICES

CROSS REFERENCE TO RELATED APPLICATIONS

This application claims the benefit of DE 102016205603.4 filed on Apr. 5, 2016, which is hereby incorporated by reference in its entirety.

TECHNICAL FIELD

Embodiments relate to a method for denoising time series images of a moved structure for medical devices. Embodiments further relate to time series images of X-ray devices.

BACKGROUND

Medical applications images may be averaged over time in order to increase the image quality. This averaging over time involves a method in which images from the same section are placed one above the other. By placing the different time series images from the same section one above the other, individual image points are overlaid, so an intensification may occur that leads to an improvement in the contrast-to-noise ratio. The improvement in the contrast-to-noise ratio contributes to an increase in the image quality. An increase in the contrast-to-noise ratio may be achieved with time series images where no movement has occurred between the individual recordings. In other words, the contrast-to-noise ratio may only occur if an image point in a first time series image is located at the same place as in the second time series image. Moved structures are located within the time series images. Averaging over the time series images leads to a loss of contrast within the regions of the moved structure.

A movement detector may be used that detects the regions in which a movement occurs. To compensate for blurring in the image in the case of a movement, averaging over the region of the moved structure is reduced or completely deactivated. Structures that have moved, are not improved in terms of visibility, for example in the contrast-to-noise ratio. Furthermore, local differences in the noise impression, for example, different artifacts may occur due to the reduced averaging in the moved regions. The current methods for denoising time series images use either fixed averaging or a method with movement detector that adjusts the degree of averaging of the movement.

SUMMARY AND DESCRIPTION

Embodiments provide a method for representing static as well as moved structures better and with an optimally high contrast-to-noise ratio.

In an embodiment, a method for denoising time series images of a moved structure for a medical device is provided. A movement detector detects the moved structure. The movement detector obtains a measurement of the similarity of images that each represent one and the same section of the moved structure. The two images originate from two different time series images. A ratio between spatial and temporal denoising is defined for the section as a function of the measurement of the similarity.

In an embodiment, an apparatus for denoising time series images of a moved structure for a medical device is provided. The apparatus includes a denoising device and a movement detector that is configured to detect the moved structure and to obtain a measurement of the similarity of images that each represent one and the same section of the moved structure. The two images originate from two different time series images. The movement detector is further configured to define a ratio between spatial and temporal denoising for the denoising device as a function of the measurement.

A multi-scalar approach may be used. The noise, for example in X-ray devices, is Poisson distributed and is convoluted with the system modulation transfer function. Signal and noise may be analyzed and processed in different spatial frequencies. To be able to improve the visibility, for example the contrast ratio, of moved structures, a time series analysis, for example of the time series images, may be applied in a multi-scalar manner. A movement detector is provided to detect the moved structure. The movement detector defines the ratio between spatial and temporal denoising using at least two different time series images, by obtaining a measurement of the similarity of the images. This movement detector may be applied to a plurality of sections. The degree of averaging is determined by the movement detector.

With a pronounced movement and subsequent low degree of temporal averaging, increased local noise may occur. A local denoiser may be used for these regions.

In an embodiment, the time series images are segmented into at least two bandpass signals. With image segmentation into bandpass signals the bandpass signals have a mean freedom. A frequency within the bandpass has an expected value of 0. After the segmentation into bandpass signals in a segmentation plane, individual denoising processes are carried out on these signals. After denoising, the denoised bandpass signals are in turn combined to form an image that is denoised thereby.

The segmentation may be a Laplace segmentation or an à trous segmentation. Both segmentations are filter methods for edge detection in frequency analysis. Appropriate edges may be detected that may not be denoised. Denoising is carried out only in the desired frequency ranges.

Segmentation may occur by an edge-preserving kernel. An increase in contrast may similarly be achieved using the edge-preserving kernel. Interference signals may simultaneously be filtered.

In an embodiment, the measurement of the similarity may be obtained using a comparison of respective output signals of one of the band passes for two of the time series images. Using the comparison of two (partial) images of the time series images, the movement detector may create a measurement of the similarity and define the ratio between spatial and temporal denoising using a decision variable. The measurement of the similarity may be obtained from more than two-time series images, for example, from three of the time series images. The comparison of a plurality of time series images may provide that a movement is detected and the measurement of the similarity is determined more reliably.

In an embodiment, the ratio between spatial and temporal denoising is applied in accordance with the following formula:

$$BP\_filtered(T)_{xy} = (1-\alpha_{xy}) \cdot BP\_denoise\_spatial(T)_{xy} + \alpha_{xy} \cdot BP\_filtered(T-n)_{x+dx, y+dy}$$

$BP\_filtered(T)_{xy}$ describes a filtered bandpass signal produced the method described above. T represents a time and here describes the current instant, while x and y describe the position of an image point in a two-dimensional coordinate system. For example, x represents the abscissa and y represents the ordinate. $\alpha_{x,y}$ may be a value between 0 and 1 and may reproduce the ratio between spatial and temporal denoising. α may indicate the magnitude of the (ad-)mixing degree for the averaging over time. The value α may be calculated, for example, using a cross-fading function. If, for example, the value α is 1, then purely temporal denoising is carried out, while α is 0, that a very high, integrated spatial denoising takes place. Temporal denoising may decrease accordingly with the admixture of spatial denoising. The function for the (ad-)mixing degree α may be a linear function, although other functions, such as, for example arctangent functions, may be used. The comparison may be formed, for example, by the sum of absolute differences. In the case of the sum of absolute differences a displacement vector may be given by the minimum of a vicinity. The sum of the local absolute difference between BP_smoothed(T,x, y) (corresponds to a spatially denoised bandpass signal before the actual method) and BP_filtered(T−1,x+dx,y+dy), for example, is formed for movement detection, so a corresponding transfer function is formed.

The value BP_denoise_spatial$(T)_{x,y}$ is a spatially denoised bandpass signal that is denoised and corresponds to BP_smoothed(T,x,y). BP_filtered$(T-n)_{x+dx,y+dy}$ is a bandpass signal similar to BP_filtered$(T)_{x,y}$, with the difference that BP_filtered$(T-n)_{x+dx,y+dy}$ is a bandpass signal from the past, and is used for comparison. The similarity of the bandpass signals is found therefore and an α is determined accordingly.

In an embodiment, the measurement of the similarity may be obtained using a comparison of respective output signals from at least two low passes for two of the images. A further increase in the accuracy of the movement detection may be achieved by the further use of low passes. The increase contributes to the image quality.

In an embodiment, the cross-fading function is a linear and/or an arctangent function. Different cross-fading functions may be used, so denoising matched to the moved structure may be achieved.

In an embodiment, the medical device is an X-ray device or an infrared recording device. Recordings of relatively large regions with moved structures may frequently occur with X-ray and infrared recording devices. The described method may improve the image quality, for example, with X-ray and/or infrared recording devices.

The scope of the present invention is defined solely by the appended claims and is not affected to any degree by the statements within this summary. The present embodiments may obviate one or more of the drawbacks or limitations in the related art.

BRIEF DESCRIPTION OF THE FIGURES

FIG. 1 depicts a block diagram of the method according to an embodiment.

FIG. 2 depicts a detailed section of FIG. 1 according to an embodiment.

FIG. 3 depicts a function profile for the value α according to an embodiment.

DETAILED DESCRIPTION

FIG. 1 depicts a block diagram of how a denoised time series image 3, 4, 5 is achieved from an image of a moved structure 9. The method corresponds to a corresponding apparatus having denoising device and movement detector. The moved structure 9 may be segmented into bandpass signals 8. The segmentation may use, for example, a Laplace segmentation or by the application of an à trous segmentation by an adaptive edge-preserving kernel. A bandpass segmentation may include a mean freedom with bandpass signals 8. Segmentation in a segmentation plane 10 into bandpass signals 8 has the property that noise, for example, in X-ray systems, is Poisson distributed and convoluted with the system modulation transfer function. The noise, but also other signals, may be analyzed and processed in different spatial frequencies. Band passes may be used. In FIG. 1 the method is carried out, for example, on only one bandpass signal 8. The method may additionally or alternatively also be applied to the other bandpass signal 8. As an alternative to segmentation into bandpass signals 8, segmentation into low-pass signals may be used. After segmentation of the moved structure 9 into different bandpass signals 8, pre-denoising is performed by a local denoiser 6 in a spatial denoising plane 17. The spatially denoised bandpass signal 12 may be produced, for example, by a measurement of the local variance in the bandpass signal 8, the comparison of this measurement with the expected variance in the noise and the reduction in local coefficients in the bandpass signal.

The spatial or spatially denoised or smoothed bandpass signal 12 is filtered further by the method 1 for movement compensation and/or movement detection. FIG. 2 depicts the method 1 in a block diagram. A movement detector 2 detects the moved structure 9 from the spatial denoised bandpass signal 12, by comparing the bandpass signal 12 spatially denoised by an image signal 14, that originates from an image buffer, at time T=T0 (with T as a whole number) with a past bandpass signal 11a at time T=T0−1, that originates from an image signal 15 at time T=T0−1 from the image buffer. Displacement vectors are produced that may be used for a decision variable 21 (cf. FIG. 3). A measurement of the similarity between the spatial denoised bandpass signal 12 at time T=T0 and the past bandpass signal 11a at time T=T0−1 may be calculated, for example, by the sum of absolute differences. In the example where the sum of the absolute differences is used as a measurement of the similarity, the displacement vector may then be given by a minimum of corresponding measurements for the similarity of the image points of a vicinity of the respective image point. The displacement vectors may also firstly be sought on low-frequency bandpass signals 8 to increase quality.

Once the movement detector 2 has calculated a degree α 23 of admixing of spatial denoising 6 in relation to temporal denoising 7 using the decision variable 21, a denoised bandpass signal 11 is output at time T=T0 14. The value of α 23 may be between 0 or 1. The value of α is described in FIG. 3, for example, as a linear transition.

In the embodiment depicted in FIG. 1 further denoised past bandpass signals 11b from the past T=T0−n 16 are also used in the method 1 in relation to the denoised past bandpass signal 11a. The use of a plurality of denoised past bandpass signals 11b provides an increase in the accuracy of the movement detection and simultaneously improves denoising.

To obtain a denoised time series image 3, the individual, partially denoised bandpass signals 11 are combined to form an image. The signals may be combined in a spatiotemporal denoising plane 18.

FIG. 3 depicts an example of how using the similarity of the sections of the moved structure 9, the movement detector chooses a decision variable 21 and calculates the ratio between spatial denoising 6 and temporal denoising 7, e.g. the value α 23. The value α 23 between 0 and 1 is depicted, in particular on the abscissa, where 0 is the origin. The decision variable 21 may be found on the ordinate, and is produced, for example, from the sums of the absolute differences of a displacement of an image point of the spatial denoised bandpass signal 12 and the past bandpass signal 11a. The profile of α 23 is depicted, by way of example, as a graph 22. The profile is linear. A low value may be found with a slight difference between the spatial denoised bandpass signal 12 and the past bandpass signal 11a, whereby α lies at 1. The degree of admixing of spatial denoising 6 is very low, for example, 0. Purely temporal denoising occurs. With a high absolute difference, α is very low, in particular (close to) 0, and high temporal denoising 7 is not applied. The decision variable 21 depicts the sum of the absolute differences. Other clearances are possible. Furthermore, other functions, that are not linear, for example an arctangent function, may be used as a graph 22. The transition point 19 (e.g. threshold value), that depicts, for example, an α 23 of 0.5, that is used for differentiation, above which clearance spatial denoising 6 or temporal denoising 7 may be applied, is used for a more detailed description of the graph 22. The steepness of the transition 20 describes the size range in which a mixing of the temporal denoiser 7 and the spatial denoiser 6 occurs and in which α 23 is not equal to 1 and not equal to 0.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for denoising a plurality of time series images of a moved structure for a medical device, the method comprising:
    detecting, by a movement detector, the moved structure;
    segmenting two images of the plurality of time series images by band passes, the two images representing a same section of the moved structure, wherein the two images originate from two different time series images of the plurality of time series images;
    obtaining, by the movement detector, a measurement of a similarity of the two images based on a comparison of respective bandpass signals of one of the band passes for the two images; and
    calculating a degree of admixing of spatial denoising in relation to temporal denoising using the measurement of the similarity,
    wherein the degree of admixing between spatial denoising and temporal denoising is applied according to the following formula:

$$BP\_filtered(T)_{x,y} = (1 - \alpha_{x,y}) \cdot BP\_denoise\_spatial(T)_{x,y} + \alpha_{x,y} \cdot BP\_filtered(T-n)_{x+dx, y+dy}$$

wherein BP_filtered(T)x,y is a denoised bandpass signal of a first of time series signals, wherein αx,y is a value between 0 and 1 and represents the degree of admixing between spatial denoising and temporal denoising, wherein the value 1 denotes solely temporal denoising and the value 0 denotes solely spatial denoising;
wherein BP_denoise_spatial(T)x,y represents a spatially denoised bandpass signal; and
wherein BP_filtered(T−n)x+dx,y+dy represents a filtered past bandpass signal of one image of the plurality of time series images preceding another image of the plurality of time series images.

2. The method of claim 1, wherein the segmenting comprises a Laplace segmentation or an à trous segmentation.

3. The method of claim 2, wherein the segmenting uses an edge preserving kernel.

4. The method of claim 3, wherein obtaining the measurement of the similarity comprises using a comparison of a respective bandpass signal of one of a band passes for the two images.

5. The method of claim 2, wherein obtaining the measurement of the similarity comprises using a comparison of a respective bandpass signal of one of a band passes for the two images.

6. The method of claim 1, wherein the measurement of the similarity is obtained using a comparison of respective output signals of at least two low passes for the two images.

7. The method of claim 1, wherein the value α is calculatable using a cross fading function, and
    wherein the cross fading function is a linear function, an arctangent function, or a linear and arctangent function.

8. The method of claim 1, wherein the medical device is an X-ray device or an infrared recording device.

9. An apparatus for denoising time series images of a moved structure for a medical device, the apparatus comprising:
    a movement detector configured to:
        detect the moved structure;
        segment two images by band pass, each of the two images representing a same section of the moved structure, wherein the two images originate from two different time series images
        obtain a measurement of a similarity of the two images from a comparison of a respective bandpass signal of one of a band passes for the two images; and
        define a degree of admixing between a spatial denoising and a temporal denoising as a function of the measurement;
    wherein the degree of admixing between spatial and temporal denoising is applied according to the following formula:

$$BP\_filtered(T)_{x,y} = (1 - \alpha_{x,y}) \cdot BP\_denoise\_spatial(T)_{x,y} + \alpha_{x,y} \cdot BP\_filtered(T-n)_{x+dx, y+dy}$$

wherein BP_filtered(T)x,y is a denoised bandpass signal of a first of the time series signals, wherein αx,y is a value between 0 and 1 and represents the degree of admixing between spatial and temporal denoising, wherein the value 1 denotes solely temporal denoising and the value 0 denotes solely spatial denoising;
wherein BP_denoise_spatial(T)x,y is a spatially denoised bandpass signal; and
wherein BP_filtered(T−n)x+dx,y+dy is a filtered past bandpass signal of one of a second time series images preceding the first.

10. The apparatus of claim 9, wherein segmenting comprises a Laplace segmentation or an à trous segmentation.

11. The apparatus of claim 10, wherein the segmenting uses an edge preserving kernel.

12. The apparatus of claim 9, wherein the movement detector is configured to obtain the measurement of the similarity using a comparison of respective output signals of at least two low passes for the two images.

13. The apparatus of claim 9, wherein the value a may be calculated by the movement detector using a cross fading function; wherein the cross fading function is a linear function, an arctangent function, or a linear function and an arctangent function.

14. The apparatus of claim 9, wherein the medical device is an X-ray device or an infrared recording device.

\* \* \* \* \*